US00PP32065P2

(12) United States Plant Patent
Grazzini

(10) Patent No.: US PP32,065 P2
(45) Date of Patent: Aug. 11, 2020

(54) ***PELARGONIUM* PLANT NAMED 'G17004'**

(50) Latin Name: *Pelargonium hybrida*
Varietal Denomination: G17004

(71) Applicant: Richard A. Grazzini, Bellefonte, PA (US)

(72) Inventor: Richard A. Grazzini, Bellefonte, PA (US)

(73) Assignee: Garden Genetics llc, Bellefonte, PA (US)

( * ) Notice: Subject to any disclaimer, the term of this patent is extended or adjusted under 35 U.S.C. 154(b) by 0 days.

(21) Appl. No.: 16/501,957

(22) Filed: Jul. 9, 2019

(51) Int. Cl.
*A01H 5/02* (2018.01)
*A01H 6/42* (2018.01)

(52) U.S. Cl.
USPC ..... Plt./324
CPC ..... *A01H 6/425* (2018.05)

(58) Field of Classification Search
USPC ..... Plt./324
CPC ..... A01H 6/425
See application file for complete search history.

*Primary Examiner* — Anne Marie Grunberg
(74) *Attorney, Agent, or Firm* — Cassandra Bright

(57) ABSTRACT

A new and distinct *Pelargonium* cultivar named 'G17004' is disclosed, characterized by light violet flowers with an orange eye, and golden foliage with a dark center. Plants are well-branched, upright with a cascading, somewhat lax habit and produce sterile flowers. The new variety is a *Pelargonium*, typically produced as an outdoor ornamental plant.

2 Drawing Sheets

Figure 1:
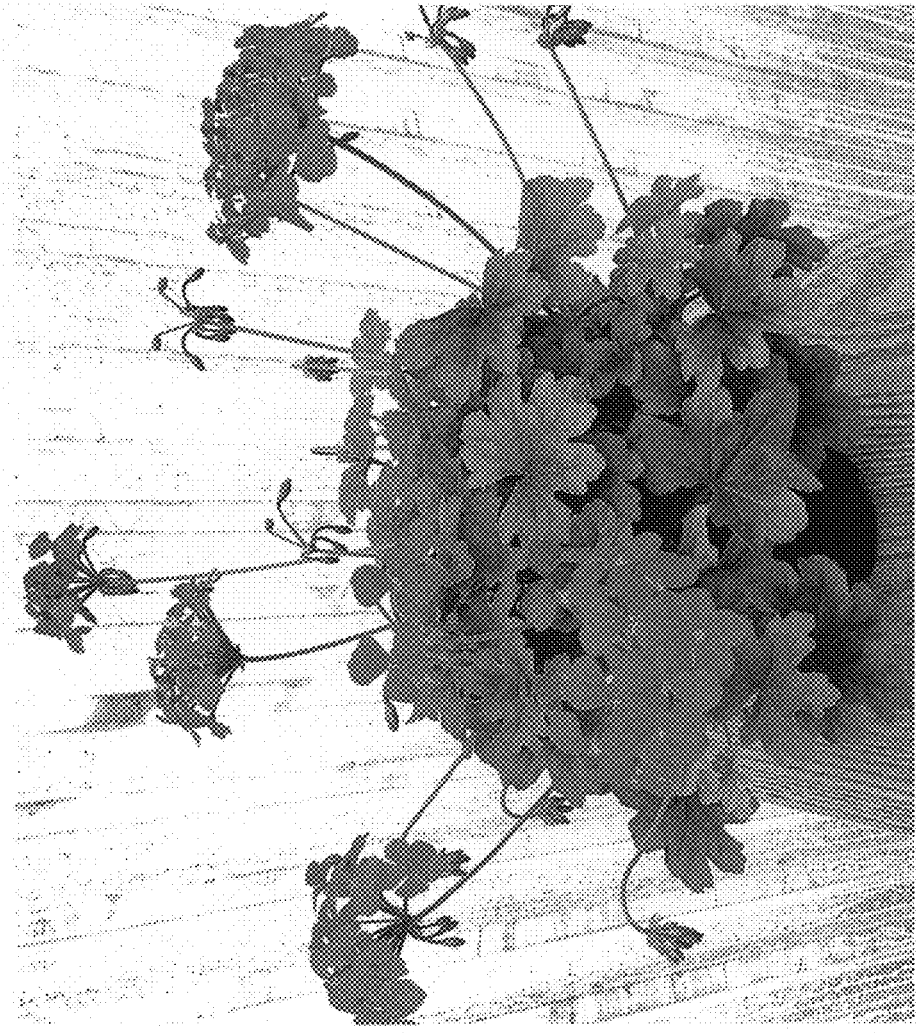

Latin name of the genus and species: *Pelargonium hybrida.*

Variety denomination: 'G17004'.

BACKGROUND OF THE INVENTION

The new cultivar is the product of a planned breeding program by the inventor, Richard A. Grazzini. The seed parent is *Pelargonium hybrida* '30806-1', unpatented. The pollen parent is *Pelargonium hybrida* '30830-2', unpatented. The crossing was made in February 2015 at a nursery in Bellefonte, Pa.

The new variety was found and selected by the inventor on Oct. 1, 2015 at the same nursery in Bellefonte, Pa. Asexual reproduction of the new cultivar 'G17004' was first performed in Bellefonte, Pa. by terminal vegetative cuttings in October 2015. Through subsequent propagation by, eight generations have been reproduced, which have shown that the unique features of this cultivar are stable and reproduced true to type. Plant material was first made available on a commercial sales basis December of 2018. This sale was made directly by the inventor or one who obtained the claimed invention directly or indirectly from the inventor. This sale and all public disclosures made between December 2018 and the filing of this application fall within the exception allowed under 102(b)(1).

SUMMARY OF THE INVENTION

The cultivar 'G17004' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'G17004'.

These characteristics in combination distinguish 'G17004' as a new and distinct *Pelargonium* cultivar:

1. Interspecific hybrid, not *hortorum.*
2. Gold-leaf.
3. Dark-centered leaf.
4. Light violet flowers with orange eye, single.
5. Densely-branched, somewhat lax (cascading) stems.
6. Sterile flowers.

PARENT COMPARISONS

Plants of the new cultivar 'G17004' are similar to the seed parent in most horticultural characteristics. The new variety, however, differs in the following ways:

1. Seed parent has rounded leaves, while the new variety is shallowly lobed.
2. Seed parent is seed and pollen-fertile, while the new variety is seed and pollen-sterile.
3. Seed parent has a more upright growth habit than the new variety.
4. Seed parent is much less densely-branched than new variety.
5. Seed parent has deep violet flowers, while the new variety has light violet flowers.

Plants of the new cultivar 'G17004' are similar to the pollen parent in most horticultural characteristics. The new variety, however, differs in the following ways:

1. Pollen parent has deeply lobed leaves, while the new variety is shallowly lobed.
2. Pollen parent is seed and pollen-fertile, while the new variety is seed and pollen-sterile.
3. Pollen parent has a lax, trailing habit, more so than new variety.
4. Pollen parent is densely branched, and more so than new variety.

5. Pollen parent has light scarlet flowers, while the new variety has light violet flowers.

COMMERCIAL COMPARISON

'G17004' is similar in most horticultural characteristics to the variety *Pelargonium hybrida* 'Cante Laver', U.S. Plant Pat. No. 18,081. The new variety, however, differs in the following ways:

1. New variety is diploid, 'Cante Laver' is tetraploid.
2. New variety has light violet flowers with an orange eye, 'Cante Laver' has lavender flowers with a white eye.
3. New variety has medium-sized single flowers, 'Cante Laver' has larger flowers.
4. New variety has gold leaves, 'Cante Laver' has green leaves.
5. Leaves of new variety have dark central blotches, 'Cante Laver' has a light colored leaf zone.

'G17004' is also similar in most horticultural characteristics to the variety *Pelargonium hybrida* 'Occold Shield', unpatented. The new variety, however, differs in the following ways:

1. New variety has single flowers, 'Occold Shield' has semi-double flowers.
2. New variety is somewhat lax, and somewhat cascading. 'Occold Shield' is upright.
3. New variety is densely branched. 'Occold Shield' is not densely branched.
4. New variety is interspecific. 'Occold Shield' is traditional x *hortorum.*
5. New variety has shallowly lobed leaves. 'Occold Shield' has rounded leaves.
6. New variety has light violet flowers. 'Occold Shield' has scarlet flowers.

BRIEF DESCRIPTION OF THE PHOTOGRAPHS

The accompanying photograph in FIG. 1 illustrates in full color a typical plant of 'G17004' grown in a greenhouse in Bellefonte, Pa. This plant is approximately 4 months old, shown planted in an 8 inch pot container.

Figure 2:
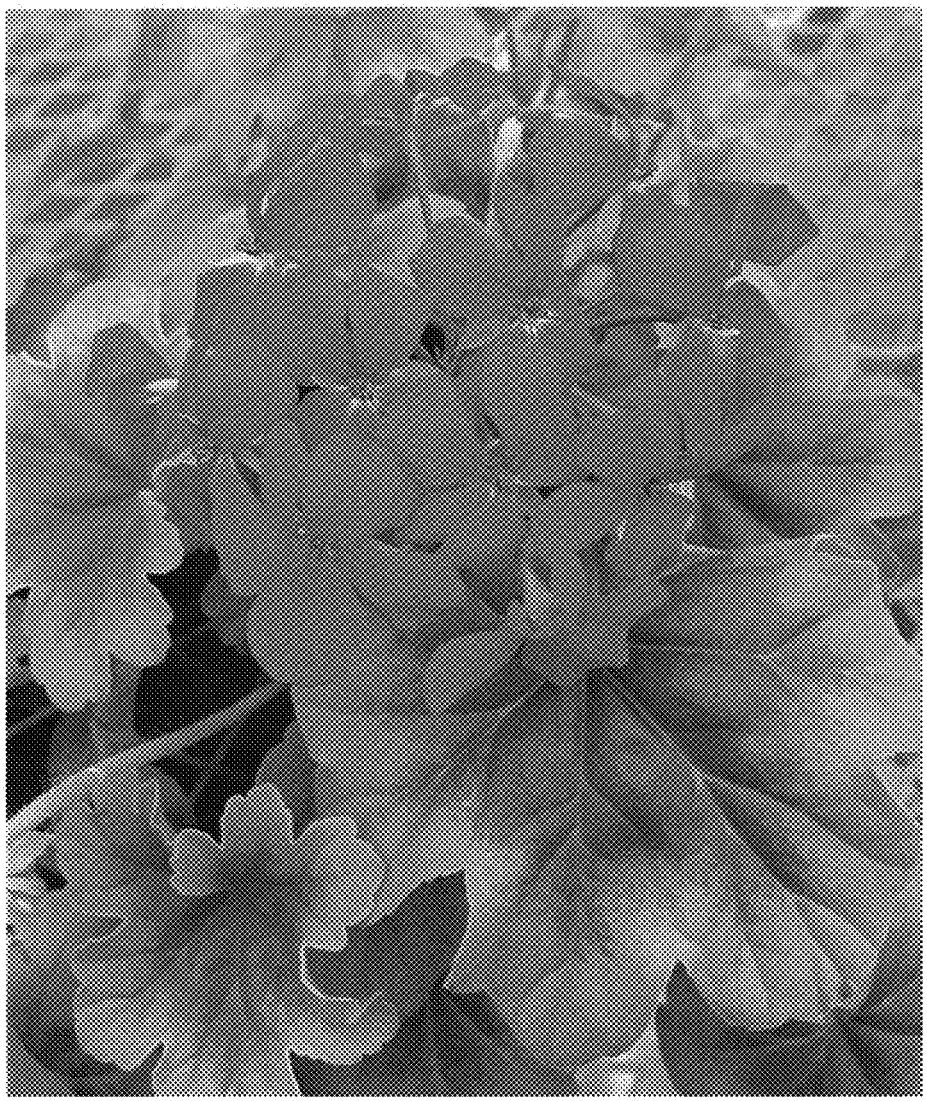

FIG. 2 illustrates in full color a close up of the flowers of 'G17004'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'G17004' plants grown to rooted cuttings in a greenhouse in Bellefonte, Pa., then flowered outdoors in Camarillo, Calif. Approximately temperatures ranged from 8° C. to 20° C. at night to 10° C. to 32° C. during the day. No artificial light, photoperiodic treatments were given to the plants. Measurements and numerical values represent averages of typical plant types.

Botanical classification: *Pelargonium hybrida* 'G17004'.

PROPAGATION

Time to initiate roots: Approximately 15 days at approximately 25° C. soil temperature.

Root description: Fine, fibrous. Color near RHS Yellow-White 158D.

PLANT

Growth habit: Upright and outwardly spreading tender perennial.

Height: Approximately 18 cm to top of foliar plane. 25 cm to highest flower.

Plant spread: Approximately 22 cm.

Pot size of plant described: 4 inch.

Growth rate: Rapid.

Branching characteristics: Well branched.

Length of primary lateral branches: Average range 4 to 8 cm.

Diameter of lateral branches: 5 mm.

Quantity of primary lateral branches: Approximately 4 to 6.

Characteristics of primary lateral branches:

*Form.*—Round.

*Color.*—Near RHS Yellow-Green 145B.

*Texture.*—Pubescent.

*Strength.*—Moderately strong.

Internode length: Average 3 mm.

Age of plant described: Approximately 6 weeks from a rooted cutting.

FOLIAGE

Leaf:

*Arrangement.*—Alternate.

*Average length* (*excluding petiole*).—Approximately 9.0 cm.

*Average width.*—Approximately 10 cm.

*Shape of blade.*—Palmate orbicular. 5 main lobes, sinuses 2.5 to 3.2 cm in depth.

*Aspect.*—Upwardly cupped.

*Apex.*—Acute to rounded.

*Base.*—Cordate.

*Margin.*—Lobed with broadly spaced crenations.

*Appearance.*—Matte.

*Texture of top surface.*—Pubescent, soft, velvety.

*Texture of bottom surface.*—Pubescent, soft.

*Color.*—Young foliage upper side: Near RHS Yellow-Green 151C, center near Greyed-Red 178A. Center coloration about 80% of lamina, stippled into Yellow-Green outer section 178A and Greyed-Orange 177A. Young foliage under side: Near RHS Yellow-Green 145C flushed 151C, center lightly stippled Greyed-Orange 177A. Mature foliage upper side: Near RHS Green 143C, center near Greyed-Orange 175C. Mature foliage under side: Near RHS Green 143C.

Venation:

*Type.*—Pinnate.

*Venation coloration upper side.*—Near RHS Yellow-Green 145A.

*Venation coloration under side.*—Near RHS Yellow-Green 145C.

Petiole:

*Length.*—Average range 8 to 14 cm.

*Width.*—Approximately 3 mm.

*Color*.—Near RHS Yellow-Green 145B.
*Strength*.—Very strong.
*Texture*.—Pubescent.

INFLORESCENCE FLOWER

Natural flowering season: Spring through Summer.
Inflorescence and flower type and habit: Single occurring flowers arranged in umbels emerging from leaf axils.
Rate of flower opening: 7 to 10 days from bud to fully opened flower.
Flower longevity on plant: About 5 to 7 days.
Persistent or self-cleaning: Self-cleaning.
Bud:
*Shape*.—Oblong.
*Length*.—Approximately 1.1 cm.
*Diameter*.—5 mm.
*Color*.—Near RHS Yellow-Green 145A.
*Texture*.—Pubescent.
Umbel size:
*Diameter*.—7.0 cm.
*Height*.—6.0 cm.
Flower size:
*Diameter*.—3.5 cm.
*Length*.—1.8 cm.
Corolla/petals:
*Arrangement*.—Rotate.
*Petal quantity*.—2 large petals, 3 small petals.
*Large petals*.—Length: 2.2 cm. Width: 1.6 cm.
*Small petals*.—Length: 1.7 cm. Width: 1.0 cm.
Petal description:
*Texture*.—Glabrous.
*Appearance*.—Matte.
*Apex*.—Obtuse.
*Base*.—Attenuate.
*Shape*.—Spatulate.
*Margin*.—Entire.
*Aspect*.—Slight upward reflex.
Color:
*When opening*.—Upper surface: Near RHS Red-Purple N57A. Lower surface: Near RHS Red-Purple N57B.
*Fully opened*.—Upper surface: Near RHS Red-Purple N57A. Lower surface: Near RHS Red-Purple N57B.
*Ageing*.—Upper surface: Near RHS Red 52A. Lower surface: Near RHS Red 52B.
Calyx/sepals:
*Quantity per flower*.—5.
*Shape*.—Narrow deltoid.
*Length*.—11 mm.
*Width*.—4 mm.
*Apex*.—Acute.
*Base*.—Truncate.
*Margin*.—Entire.
*Texture*.—Pubescent, velvety all surfaces.
*Color*.—Upper Surface: Near RHS Yellow-Green 145B. Lower Surface: Near RHS Yellow-Green 145B.
Peduncle:
*Length*.—Average range 10 to 15 cm.
*Diameter*.—Approximately 3 mm.
*Color*.—Near RHS Yellow-Green 145B.
*Texture*.—Pubescent.
*Strength*.—Strong.
*Orientation*.—Approximately 15 to 45 degree angle from leaf axil.
Pedicel:
*Length*.—Average 3.0 cm.
*Diameter*.—Approximately 2 mm.
*Color*.—Near RHS Red 47D.
*Texture*.—Pubescent.
*Strength*.—Moderate, flexible.
*Orientation*.—Approximately 15 degree angle from peduncle.
Fragrance: Musty.

REPRODUCTIVE ORGANS

Stamens:
*Number*.—5.
*Filament length*.—About 3 mm.
Anthers:
*Shape*.—Linear, strongly recurved.
*Length*.—Abut 2 mm.
*Color*.—Near RHS Red-Purple 61B.
*Pollen*.—Not observed.
Pistil:
*Number*.—1.
*Length*.—Approximately 3 mm.
*Style*.—Length: 1 mm. Color: Near RHS Green-White 157A.
*Stigma*.—Shape: 5 parted linear. Color: Near RHS Red-Purple 61B.
*Ovary*.—Ovary Color: Near RHS Yellow-Green 145C. Ovary length: Approximately 2 mm.

OTHER CHARACTERISTICS

Disease resistance: Neither resistance nor susceptibility to the normal diseases and pests of *Pelargonium* has been observed.
Drought tolerance and cold tolerance: The new cultivar can tolerate cold temperatures to approximately −1° C. and tolerates an upper temperature range to at least 38° C.
Fruit/seed production: Not observed to date.

What is claimed is:

1. A new and distinct cultivar of *Pelargonium* plant named 'G17004' as herein illustrated and described.

* * * * *